US00PP27750P3

(12) United States Plant Patent
Suzuki

(10) Patent No.: US PP27,750 P3
(45) Date of Patent: Mar. 7, 2017

(54) ***LOROPETALUM* PLANT NAMED 'KURENAI'**

(50) Latin Name: *Loropetalum chinense*
Varietal Denomination: KURENAI

(71) Applicant: Yuji Suzuki, Kawaguchi (JP)

(72) Inventor: Yuji Suzuki, Kawaguchi (JP)

(73) Assignee: Spring Meadow Nursery, Inc., Grand Haven, MI (US)

( * ) Notice: Subject to any disclaimer, the term of this patent is extended or adjusted under 35 U.S.C. 154(b) by 83 days.

(21) Appl. No.: 14/544,869

(22) Filed: Feb. 26, 2015

(65) Prior Publication Data

US 2016/0262293 P1 Sep. 8, 2016

(51) Int. Cl.
*A01H 5/00* (2006.01)

(52) U.S. Cl.
USPC ..... Plt./226

(58) Field of Classification Search
USPC ..... Plt./226
See application file for complete search history.

*Primary Examiner* — Susan McCormick Ewoldt
*Assistant Examiner* — Karen Redden
(74) *Attorney, Agent, or Firm* — Cassandra Bright

(57) ABSTRACT

A new and distinct *Loropetalum* cultivar named 'KURENAI' is disclosed, characterized by deep red foliage and bright pink flowers. Dwarf, mounded form and a bright red Fall color. The new variety is a *Loropetalum*, normally produced as an outdoor garden or container plant.

2 Drawing Sheets

Figure 1:
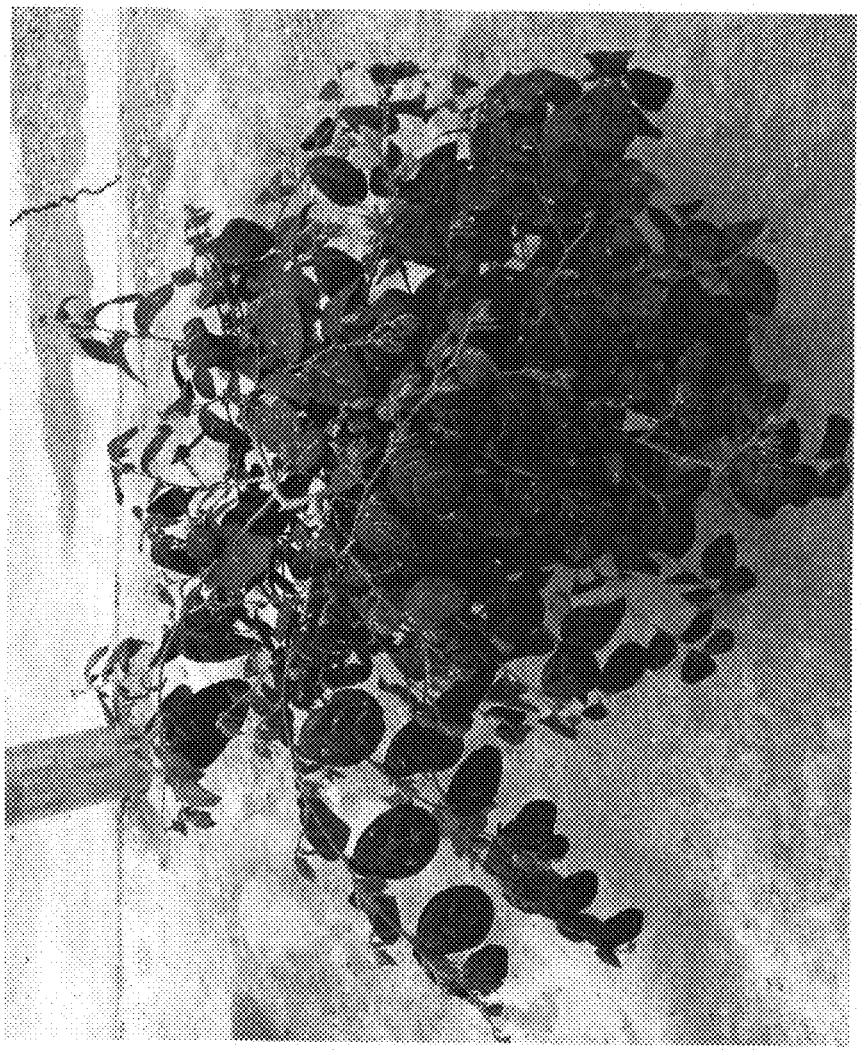

Latin name of the genus and species: *Loropetalum chinense*.

Variety denomination: 'KURENAI'.

BACKGROUND OF THE INVENTION

The new *Loropetalum* cultivar is a product of a planned breeding program conducted by the inventor, Yuji Suzuki, in Kawaguchi City, Saitama, Japan. The objective of the breeding program was to produce new *Loropetalum* varieties with better foliage color and improved flowering for ornamental commercial applications. The cross resulting in this new variety was made during Apr. 20, 2005.

The seed parent is the, unpatented, commercial variety referred to as *Loropetalum* 'Kurohikari'. The pollen parent is the unpatented, variety *Loropetalum* '8-21'. The new variety was discovered in a commercial nursery by the inventor in a group of seedlings resulting from the 2005 crossing, in Kawaguchi City, Saitama, Japan.

Asexual reproduction of the new cultivar was performed by softwood cuttings. This was first performed at a commercial nursery in Kawaguchi City, Saitama, Japan, in 2011 and has shown that the unique features of this cultivar are stable and reproduced true to type in 5 successive generations.

SUMMARY OF THE INVENTION

The cultivar 'KURENAI' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'KURENAI' These characteristics in combination distinguish 'KURENAI' as a new and distinct *Loropetalum* cultivar:

1. Attractive deep red foliage.
2. Attractive bright red fall foliage color.
3. Bright pink flowers.
4. Dwarf, mounded habit (1-3' tall).

Plants of the new cultivar 'KURENAI' are similar to plants of the seed parent, *Loropetalum* 'Kurohikari' in most horticultural characteristics, however, plants of the new cultivar 'KURENAI' differ in the following;

1. Bright pink flowers. The parent has dark red flowers.
2. Bright red Fall foliage. The parent's foliage has no significant fall color change.
3. Spreading, mounding growth habit. The parent growth habit is spreading.
4. Underside of foliage is darker red in the new variety.

Plants of the new cultivar 'KURENAI' are similar to plants of the pollen parent, *Loropetalum* '8-21' in most horticultural characteristics, however, plants of the new cultivar 'KURENAI' differ in the following;

1. Bright pink flowers. The parent has lighter red/pink flowers.
2. Bright red Fall foliage. The parent's foliage has no significant fall color change.
3. Spreading, mounding growth habit. The parent's growth habit is spreading.
4. The new variety foliage color is darker.

COMMERCIAL COMPARISON

Plants of the new cultivar 'KURENAI' are comparable to the patented, commercial variety *Loropetalum* 'Peack' U.S. Plant Pat. No. 18,441. The two *Loropetalum* varieties are similar in most horticultural characteristics; however, the new variety 'KURENAI' differs in the following:

1. Tight mounded habit. The Comparator growth habit is mounded and outward spreading.
2. Less spread in growth habit.

3. Bright pink flowers. The comparator has flowers that are more red in color.

BRIEF DESCRIPTION OF THE PHOTOGRAPHS

The accompanying photograph in FIG. 1 illustrates in full color a typical plant of 'KURENAI' grown in a 1 gallon pot. Age of the plant photographed is approximately 1 to 2 years old from a rooted cutting.

Figure 2:
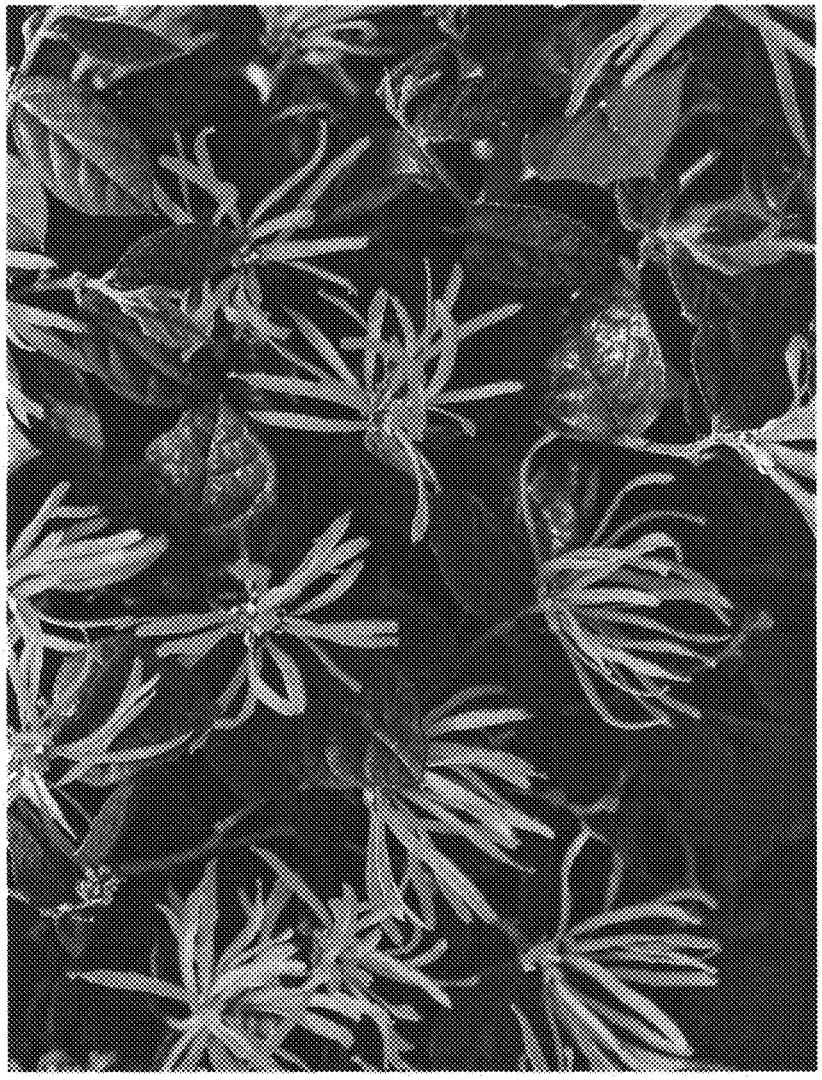

FIG. 2 illustrates a close up of the foliage and flowers.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007 except where general terms of ordinary dictionary significance are used. The following observations and measurements describe 'KURENAI' plants grown in a greenhouse, in Grand Haven Mich. The growing temperature averaged from 60-65° F. during the day and from 40-50° F. during the night. Growing conditions are double poly from Fall through Winter heated to 35° F. The poly was removed in the Spring. Shade cloth through the summer. Measurements and numerical values represent averages of typical plant types. Botanical classification: *Loropetalum* 'KURENAI'.

PROPAGATION

Type of propagation typically used: Cutting.
Time to initiate roots: 18 days at 27° C.
Number of days to produce a rooted liner in summer: 110 days at 27° C.
Root description: Medium to thick, fibrous, free branching. Young growth tends to be fleshy. Roots are purple in color.

PLANT

Type of plant: Perennial shrub.
Age of plant described: Approximately 1-2 years old.
Container size of the plant described: 1 gallon.
Appropriate containers sizes: 1 and 2 gallon nursery containers.
Growth habit: Rounded, mounded.
Height: 12-36 inches.
Plant spread: 12-36 inches.
Growth rate: Moderate to rapid.
Plant vigor: Good.
Branching characteristics: Lateral, some basal branching.
Pinching required: Yes, increases branching.
Characteristics of primary lateral branches:
- *Length.*—19 cm.
- *Shape.*—Round.
- *Quantity.*—12.
- *Diameter.*—2.5-3.0 mm. Color: Young stems: Near RHS Brown 200B. Older stems: Near RHS Brown 200D.
- *Aspect:* 0-30°.
- *Strength.*—Good.

Internode length: 1.68 cm.
Stem pubescence: Yes.

FOLIAGE

Leaf:
- *Arrangement.*—Alternate, Single.
- *Quantity.*—Approximately 15-20 per branch.
- *Average length.*—2.1-4.6 cm.
- *Average width.*—1.6-3.2 cm.
- *Shape of blade.*—Ovate, rounded.
- *Tip.*—Acute.
- *Base.*—Oblique.
- *Margin.*—Entire.
- *Texture of top surface.*—Rough due to pubescence. Pubescence is heavier on young leaves, and only slight on older leaves.
- *Texture of bottom surface.*—Ribbed due to protruding veins, slight to moderate pubescence.
- *Color.*—Young foliage describes Spring coloration. Mature foliage describes Summer coloration. Fall Color: Upper side: Near Grey-Green 197A with Greyed-Red 178A and 178C. Greyed-Orange 171A and 163C present irregularly. Spotted Green 141B. Under side: Glaucous, near Grey-Green 197A with Greyed-Red 178A. Young foliage upper side: Near RHS Greyed-purple 187B. Young foliage under side: Near RHS Red-purple 59A. Mature foliage upper side: Near RHS Black 202A with overtones of Greyed-purple 187A. Mature foliage under side: Glaucous. Near RHS Red-purple 59A.
- *Venation.*—Type: Pinnate. Venation color upper side: Midribs and veins are depressed on the upper side. Color same as the leaf color. Venation color under side: Midribs and veins are prominent on the underside. Near RHS Greyed-purple 186A.
- *Petiole.*—Length: 0.2 to 0.4 cm. Diameter: 1 mm. Color: Near RHS Greyed-purple 183A.
- *Durability of foliage to stress.*—Good.

FLOWER

Inflorescence and flower type and habit: Perfect flowers, comprised of strap-shaped petals, occurring in terminal (mainly) and axillary (occasionally) umbels.
Quantity of flowers per inflorescence: 5.
Flower type: Perfect, self-cleaning flowers made up of linear petals.
Flower aspect: Upright and outward.
Quantity of flowers per lateral stem: 14-30.
Quantity of flowers per plant: 60-500, depending on maturity.
Natural flowering season: Spring.
Fragrance: None.
Bud:
- *Shape.*—Obovate.
- *Length.*—2 mm.
- *Diameter.*—2 mm.
- *Color.*—Top of bud: Near RHS Red-purple 59A. Base of bud: Near RHS Red-purple 60C.

Petals:
- *Quantity per flower.*—4.
- *Shape.*—Linear.
- *Margin.*—Entire.
- *Texture.*—Smooth, silky.
- *Appearance.*—Ribbon-like.
- *Length.*—1.8-2.0 cm.

*Width.*—2-3 mm.
*Tip.*—Truncate.
*Color.*—When opening: Upper surface: Near RHS Red-purple 61A. Lower surface: Near RHS Red-purple 61A. Fully opened: Upper surface: Near RHS Red-purple 61A. Lower surface: Near RHS Red-purple 61A. Petal color fading to: Near RHS Red-purple 61A.

Sepals:
*Quantity per flower.*—4.
*Appearance.*—Slightly glaucous and pubescent.
*Arrangement.*—Whorl.
*Shape.*—Ovate and fused, slightly curled outward.
*Length.*—4 mm.
*Width.*—2 mm.
*Tip.*—Slightly reflexed.
*Base.*—Fused.
*Margin.*—Entire, smooth.
*Color.*—Immature upper and lower side: Near RHS Red-purple 60A. Mature upper and lower side: Near RHS Red-purple 58A.

REPRODUCTIVE ORGANS

Stamens: Number: 4.
Pistil: Number: 2.

OTHER CHARACTERISTICS

Lowest temperature tolerant to: 5 to 10° F.
Disease/pest resistance: No unusual susceptibility to diseases or pests noted to date.
Fruits and seeds: Rarely observed. If produced, capsule size is approximately 9 mm long by 7 mm wide. Mature capsule colored between Greyed-Brown 199B and Greyed-Orange 174B. Very few seeds observed within capsule.
Drought tolerance: Moderate to good drought tolerance once established.

What is claimed is:

1. A new and distinct cultivar of *Loropetalum* plant named 'KURENAI' as herein illustrated and described.

* * * * *